United States Patent [19]

Brown et al.

[11] Patent Number: 5,176,700
[45] Date of Patent: Jan. 5, 1993

[54] LAPAROSCOPIC SPONGER-DISSECTOR FORCEPS

[75] Inventors: Michael A. Brown, Bluemont; Joseph P. McWhinney, Millwood, both of Va.

[73] Assignee: POD, Inc., Boyce, Va.

[21] Appl. No.: 643,267

[22] Filed: Jan. 22, 1991

[51] Int. Cl.$^5$ ............................................. A61B 17/42
[52] U.S. Cl. ................................. 606/206; 606/207; 294/100
[58] Field of Search ................................ 606/205–210, 606/120–124, 190, 151, 157–158, 139–142, 133; 433/159; 294/99.1, 99.2, 100

[56] References Cited

U.S. PATENT DOCUMENTS

| | | | |
|---|---|---|---|
| 1,036,725 | 8/1912 | Sabo | 606/133 |
| 1,151,583 | 8/1915 | Hanson | 606/122 |
| 1,682,621 | 8/1928 | Leneschmidt | 606/124 |
| 2,898,915 | 8/1959 | Kammer | 606/139 |
| 2,898,916 | 8/1959 | Kammer | 606/139 |
| 3,777,760 | 12/1973 | Essner | |
| 4,192,313 | 3/1980 | Ogami | |
| 4,374,523 | 2/1983 | Yoon | 606/140 |
| 4,467,802 | 8/1984 | Maslanka | 294/100 |
| 4,592,347 | 6/1986 | Mahruki | |
| 4,646,751 | 3/1987 | Maslanka | 606/208 |
| 4,940,454 | 7/1990 | Siragusa | |
| 5,026,379 | 6/1991 | Yoon | 606/141 |

Primary Examiner—C. Fred Rosenbaum
Assistant Examiner—Ronald Stright
Attorney, Agent, or Firm—Laurence R. Brown

[57] ABSTRACT

This invention provides an improved surgical instrument, namely sponger-dissector forceps particularly adapted for laparoscopic intra-abdominal surgery such as gall bladder removal. Thus, sponges are retained locked in place without manual force upon the distal end of a substantially cylindrical hand held assembly by means of an internally mounted ratchet mechanism. In one embodiment sponges are retained by a 7 shaped distal end on a reciprocating 2 mm diameter rod disposed in a 10 mm diameter cylindrical housing member. The ratchet locks the reciprocating rod in place against movement in the distal direction, and thus holds sponges clamped in place at the distal end. The ratchet lock is releasable by a catch release button. The rod is manually reciprocated to engage and clamp a sponge by a finger operated slide member. The sponge is thus firmly held in position for blunt manipulation including direct hemostasis pressure on small blood vessels or for sponging to keep the surgical region dry. A clamping jaw embodiment provides for holding a sponge or alternatively for using the instrument for dissection or as a blood vessel clamp. Thus, tissue in an abdominal cavity may be grasped, displaced, or removed by manual manipulation from outside the body.

8 Claims, 1 Drawing Sheet

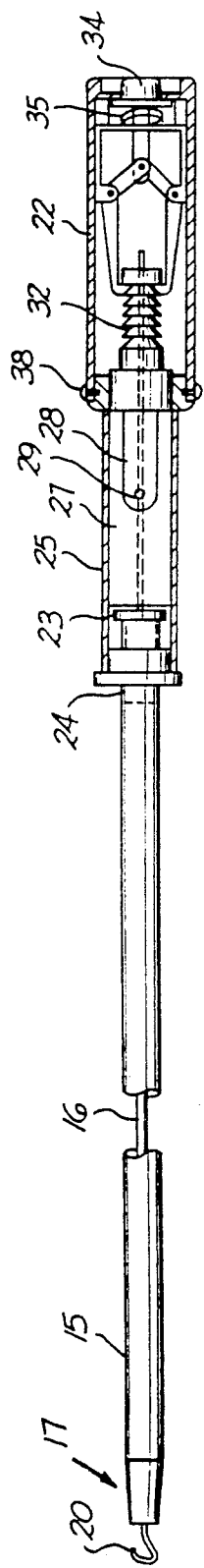
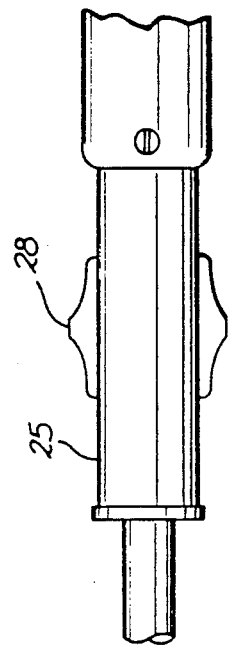
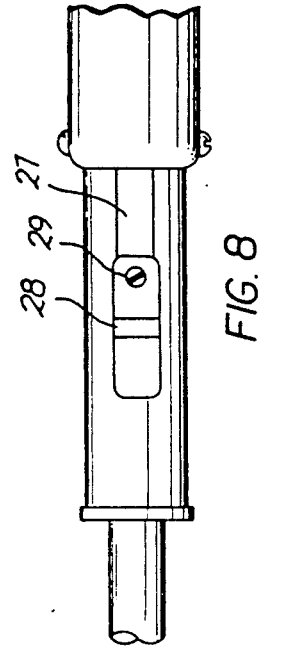
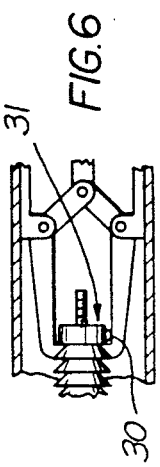
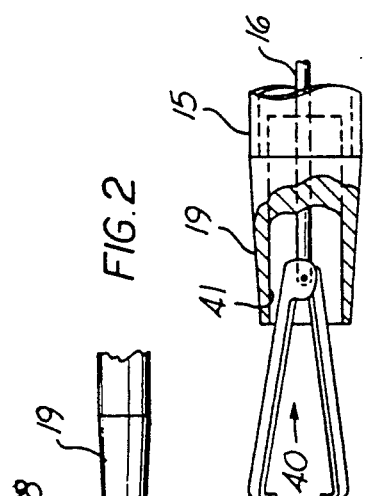
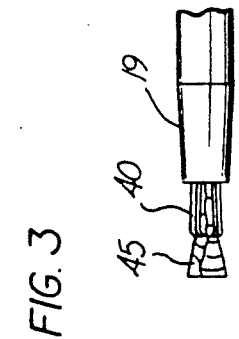
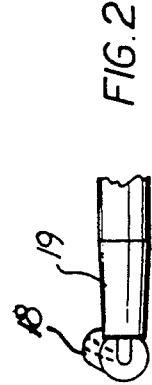

LAPAROSCOPIC SPONGER-DISSECTOR FORCEPS

FIELD OF THE INVENTION

This invention relates to surgical instruments and more particularly it relates to forceps for use in laparoscopic surgery, such as for intra-abdominal gall bladder surgery and the like, as blunt instruments, as dissector or grasper clamps, and for carrying sponges for removal of blood and fluids and for hemostasis.

BACKGROUND ART

In laparoscopic surgery special instrumentation is required that can be manipulated from outside the body through small incisions. In particular, blunt instruments are required for pushing back tissue or organs for viewing or out of the way of surgical procedures, and sponges are required for hemostasis and for removing fluids to obtain a better view of critical regions. During surgical procedures organs and tissues need to be grasped for displacement or removal by dissectors. These instruments need to be manipulated from outside the body. Dimensions are critical to give the proper reach and to be inserted through small incisions in the abdomen, for example.

For handling such functions as pushing back tissue or hemostasis of particular small blood vessels, the instruments need to be well balanced and easily and surely held without the necessity for other functions in the operation of the forceps such as required for holding sponges in place by manual clamping of jaws. The instruments must be used and reused under sterile conditions and thus need to be constructed for ready disassembly and sterilization.

Surgical sponge holders and retraction instruments are known generally in the art. Thus N. M. T. Mahruki in U.S. Pat. No. 4,592,347, Jun. 3, 1986 provides an instrument for removing vaginal sponges. This instrumentation is critical to manual operation of clamping members inside the body and is not adapted to the multifunction surgical procedures in laparoscopic surgery where hand manipulated instruments must permit the surgeon and assistant freedom of the hands and brain as much as possible for the surgery without detraction from auxiliary chores. Similarly forceps for insertion of sponges and the like as set forth in U.S. Pat. Nos. 4,192,313, N. Ogami, Mar. 11, 1980; and 4,940,454, A. Siragusa, Jul. 10, 1990 disclose instruments requiring critical usage of the hands in a manner inconsistent with the laparoscopic surgery environment. H. Essner in U.S. Pat. No. 3,777,760, Dec. 11, 1973, has disclosed a sponge holder that locks in place a sponge for use in surgical procedures. This does not require manipulation of jaws or sponge holders or retrievers, and is advantageous in that respect. However, it does not assure secure enough grasping of sponges that may vary slightly in size or shape to prevent the danger of loss of sponges when used as blunt manipulation in laparoscopic surgery, for example.

All of the foregoing instruments are special purpose sponge holding instruments. None are suitable for alternative use as dissectors in laparoscopic surgery with simple manual jaw manipulation from outside the body to grasp and displace or remove tissue.

Accordingly it is a primary objective of this invention to provide improved and versatile instrumentation particularly adapted to laparoscopic surgical procedures.

Other objects, features, and advantages of the invention will be found throughout the following description, drawings and claims.

BRIEF DISCLOSURE OF THE INVENTION

Thus, a multipurpose laparoscopic instrument is provided by this invention, namely dissector-sponger forceps of small diameter for insertion in a small incision in the abdomen and having a length for probing intra-abdomen locations, for example. There is provided a variably positionable locked-in-place ratcheting mechanism adapted to either be pre-loaded for grasping a sponge or for manipulation outside the body for dissection functions in the surgical procedure.

Thus a small diameter (2 mm) rod is reciprocated manually within a generally cylindrical body from about 30 to 50 cm in length by means of a manually operable slide on the proximal end of the cylinder. The rod is connected to a ratcheting mechanism, which has a releasable push button operated catch mechanism for variably adjusting the reciprocal position of the rod, such as for the purpose of clamping a sponge, or grasping tissue in the intra-abdominal cavity during laparoscopic surgery by means of distal end clamping structure manipulated by the rod. Thus the instrument may be used as a preloaded clamp for a sponge or alternatively as a dissector with locking clamping jaws that may be manipulated manually from outside the body during laporoscopic surgery.

BRIEF DESCRIPTION OF THE DRAWINGS

The instrumentation afforded by this invention will be better understood by reference to the accompanying drawings, in which similar reference characters refer to similar features throughout the several views, wherein:

FIG. 1 is a side view sketch, partly broken away of one embodiment of the invention;

FIG. 2 is a fragmental view, partly in perspective, of the operation of this embodiment as a sponger instrument;

FIG. 3 is a fragmental view of an alternative dissector jaw type of distal end configuration of the instrument of FIG. 1;

FIGS. 4 and 5 respectively show a sponge before and after clamping by the dissector jaws in the sponging configuration;

FIG. 6 is a fragmental portion of the FIG. 1 embodiment illustrating a feature for adjustment of the length of the movable rod assembly; and FIGS. 7 and 8 are fragmental views of the FIG. 1 embodiment showing manually operable rod reciprocating controls.

THE PREFERRED EMBODIMENT

The sponger instrument embodiment shown in FIG. 1 has a generally hollow cylindrical housing 15 inside which a rod 16 of 2 mm diameter reciprocates. The diameter of the cylindrical housing at the distal end is ten mm. The distal end region 17, also shown in FIG. 2, has a tapered snout through which extends a 7 shaped tip 20 of the reciprocatable rod 16. That tip 20 has a laterally extending arm for mating in a mounting cavity in a cylindrical shaped sponge 18 which is held in a seated position against the snout 19 when the reciprocatable rod 16 is retracted. Typically the sponge is a generally spherical sterile surgical sponge with a ⅜ inch diameter and a pierced axial cavity.

The rod 16 is retained and reciprocated by the mechanism in the proximal end handle region 22 of the housing. Thus, the rod 16 passes through a sterile seal plug 23 having a ten mm diameter extension 24 fitting into the distal end cylinder 15 at the transition joint with the distal end cylinder 25. Screw threads 26 on the proximal end of the rod 16 are threaded into mating threads axially disposed in a core member 27, which is manually reciprocated by the finger or thumb slide 28, also shown in FIGS. 7 and 8, outside the housing section 25 affixed by screw 29 to the core member 27. As seen in FIG. 6, somewhere along the length of the rod 16, such as the end portion, the shaft is flattened at 31 for receipt of a set screw 30. Thus the housing may be rotated while the tip is pressing against a target area without changing the effective adjusted length of the rod 16.

The core member has affixed thereto at the proximal end a set of ratchet teeth 32, which are retained by the releasable ratchet catch assembly 33. Thus when the button 34, biased by spring 35 to keep the catch in engagement with a ratchet tooth 32, is manually depressed the yoke 36 opens the catch arms to release the rod for movement in the distal direction by means of slide 28. When slide 28 is moved in the proximal direction, the ratchet mechanism locks the rod position into place with catch 33 engaging a corresponding ratchet tooth 32. Thus the 7 shaped tip 20 may be extended to receive the sponge 18 and retracted to seat it firmly against the tip of snout 19 for use in the conventional manner as a sponge at a work site. Also the sponge may serve as a blunt instrument for pushing aside tissue or organs for better viewing in a laparoscopic procedure.

The handle portion of the housing 22 is affixed by screws 38 so that the instrument may be disassembled for adjustment of the rod 16 length, sanitation or for replacement of seal 23, etc. The catch assembly 33, resident in the handle portion 22, thus is released by button 34 to remove the handle 22 from the instrument.

The range of reciprocation of rod 16 is fixed by the abutting of core member 27 against seal 23 in the distal direction of movement and by engagement of the tip 20 or its retained sponge with the snout 19 in the proximal direction of movement.

It is seen thus that the instrument is well balanced and easily hand manipulated so that the distal end may be inserted into a small incision in the abdomen, for example, and manipulated within the intra-abdomen region in a laparoscopic surgery procedure.

Another embodiment of the distal end region of the instrument is shown in FIGS. 3, 4 and 5. The end of the rod 16 in this embodiment is affixed to a set of jaws 40, normally biased open by a spring, not shown, or by construction from spring stock. Thus, when extended out of the snout inner bore nest 41, the jaws open as shown in FIG. 3 and when the rod 16 is retracted the tip of the snout 19 frictionally engages the jaws and clamps them together. The jaws are critically sized to grasp in working position a sponge 45 typically of ¼ inch diameter and 9/16 inch length, and to firmly hold it in place without any danger of losing it when sponging or using the sponge as a blunt instrument.

This embodiment has the advantage of alternative operation as a dissector instrument, since the clamping jaws 40 may be manipulated manually for grasping tissue or organs for movement within the abdominal cavity for better viewing or for removal. Also the jaws may be used to clamp a blood vessel for example, since they are locked in place at a variable position by the ratchet teeth and thus can free a hand for other use in a surgical procedure.

Having therefore introduced a novel instrument with various advantages and functions useful in the art of laporoscopic surgical procedure, those features of novelty setting forth the spirit and nature of the invention are defined with particularity in the following claims.

We claim:

1. A multipurpose laparoscopic instrument useful for blunt manipulation and sponging of intra-abdominal tissue, comprising in combination, an elongate substantially cylindrical housing adapted to be held by hand, of a length exceeding 30 cm and of a distal end diameter of about 10 mm, means for reciprocally sliding a rod within the housing over a limited range of movement, sponge holding means positioned on a distal end of the rod for grasping and retaining a sponge in response to reciprocal movement of the rod within the housing, and ratcheting means disposed within a proximal end of said housing comprising ratchet teeth disposed on a member slidably movable with said rod and a ratchet teeth catch mechanism operable manually from a position outside the housing, wherein the sponge holding means clamps and holds a sponge firmly in place at the distal end of the rod in a retracted position of the rod established by the ratchet teeth catch engagement with the ratchet teeth and releases the sponge when the catch is manually released and the rod is extended, and wherein said sponge holding means further comprises a pair of jaw members for movement with reciprocation of the rod and having a mechanism operable in the distal end of the housing to open the jaws in an extended position of the rod and to close them in a clamping position in a retracted position of the rod.

2. The instrument of claim 1 wherein said jaw members are dimensioned for grasping and retaining cylindrical shaped sponges with a ¼ inch diameter and a length of 9/16 inch.

3. A multipurpose laparoscopic instrument useful for blunt manipulation and sponging of intra-abdominal tissue, comprising in combination, an elongate substantially cylindrical housing adapted to be held by hand, of a length exceeding 30 cm and of a distal end diameter of about 10 mm, means for reciprocally sliding a rod within the housing over a limited range of movement, sponge holding means positioned on a distal end of the rod for grasping and retaining a sponge in response to reciprocal movement of the rod within the housing, and ratcheting means disposed within a proximal end of said housing comprising ratchet teeth disposed on a member slidably movable with said rod and a ratchet teeth catch mechanism operable manually from a position outside the housing, wherein the sponge holding means clamps and holds a sponge firmly in place at the distal end of the rod in a retracted position of the rod established by the ratchet teeth catch engagement with the ratchet teeth and releases the sponge when the catch is manually released and the rod is extended, and wherein said sponge holding means further comprises a pair of jaw members for movement with reciprocation of the rod and having a mechanism operable in the distal end of the housing to open the jaws in an extended position of the rod and to close them in a clamping position in a retracted position of the rod, wherein said sponge holding means further comprises a 7 shaped configuration of the distal end of the rod with a laterally extending arm for mating in a mounting cavity of a sponge and with a seating structure at the end of the cylindrical housing for engaging and seating sponges when the rod is retracted.

4. The instrument of claim 3 wherein the sponge holding means is dimensioned for engaging and clamping in place on said seating structure ⅜ inch diameter sponges with a pierced central hole.

5. A multipurpose laparoscopic instrument useful for blunt manipulation and sponging of intra-abdominal tissue, comprising in combination, an elongate substantially cylindrical housing, adapted to be held by hand, of a length exceeding 30 cm and of a distal end diameter of about 10 mm, means for reciprocally sliding a rod within the housing over a limited range of movement, sponge holding means positioned on a distal end of the rod for grasping and retaining a sponge in response to the reciprocal movement of the rod within the housing, ratcheting means disposed within a proximal end of said housing comprising ratchet teeth disposed on a member slidably movable with said rod and a ratchet teeth catch mechanism operable manually from a position outside the housing, wherein the sponge holding means clamps and holds a sponge firmly in place at the distal end of the rod in a retracted position of the rod established by the ratchet teeth catch engagement with the ratchet teeth and releases the sponge when the catch is manually released and the rod is extended, and a proximal end housing portion of greater diameter than 10 mm in which the ratchet teeth are disposed and means coupling the proximal portion of the 10 mm diameter cylindrical housing at a transition joint retaining a sterile seal plug for engaging said rod and fitting into the distal end housing portion.

6. The instrument of claim 5 further comprising a limiting stop for movement in an extended direction of reciprocation of said rod formed by the engagement of said coupling assembly with said seal.

7. The instrument of claim 5 further comprising a coupling assembly reciprocally movable within said proximal end housing portion coupling a threaded proximal end of said rod to the ratchet teeth by means of a threaded axial cavity in the member slidably movable with the rod.

8. The instrument of claim 7 further comprising a flattened surface on the proximal end of the threaded rod, and a set screw engaging said flattened surface to hold the rod in place when screwed into said coupling assembly.

* * * * *